United States Patent [19]

Mauldin et al.

[11] 4,370,977
[45] Feb. 1, 1983

[54] KNEE AND ELBOW BRACE

[75] Inventors: Donald M. Mauldin; Richard E. Jones, III, both of Dallas, Tex.

[73] Assignees: Kenneth D. Driver, Dallas; Melvin L. Stills, Lewisville, both of Tex.; part interest to each

[21] Appl. No.: 260,075

[22] Filed: May 4, 1981

[51] Int. Cl.³ .............................................. A61F 3/00
[52] U.S. Cl. ..................................... 128/80 F; 128/88
[58] Field of Search ................. 128/80 F, 80 E, 80 C, 128/80 R, 88, 87 R, 83

[56] References Cited

U.S. PATENT DOCUMENTS

| | | | |
|---|---|---|---|
| 1,072,369 | 9/1913 | Spahn | 128/80 F |
| 1,939,097 | 12/1933 | Bauman | 128/80 F |
| 2,267,848 | 12/1941 | Talyor | 128/80 E |
| 2,410,560 | 11/1946 | Witte | 128/80 F X |
| 2,536,454 | 1/1951 | McIntyre | 128/80 E |
| 2,567,195 | 9/1951 | Ellery | 128/80 E |
| 2,632,440 | 3/1953 | Hauser et al. | 128/80 F |
| 2,883,982 | 4/1959 | Rainey | 128/80 F |
| 3,528,412 | 9/1970 | McDavid | |
| 3,732,861 | 5/1973 | Lehneis | 128/80 F X |
| 3,779,654 | 12/1973 | Horne | 128/80 C X |
| 3,853,123 | 12/1974 | Moore | |
| 3,935,858 | 2/1976 | Harroff | |
| 4,088,130 | 5/1978 | Applegate | |

FOREIGN PATENT DOCUMENTS 813501  5/1959  United Kingdom .

Primary Examiner—John D. Yasko
Attorney, Agent, or Firm—Richards, Harris & Medlock

[57] ABSTRACT

An improved knee brace (10) is disclosed. The knee brace includes thigh and calf cuffs (12, 14) and identical side members (15, 16) to simplify manufacture and permit use with a range of leg sizes. The hinge members (24) on each of the side members permit the knee joint to be immobilized at a predetermined degree of flexion or movable within a predetermined arc of motion such as 0° to 30° flexion or 30° to 60° flexion. A tensioned cord (70) is provided to urge the knee joint in a given direction. The spring force may be employed to inhibit the quadriceps muscles or permit progressive resistance exercises during rehabilitation. In a first modification, a torsion spring (250) replaces the tension cord (70) and forms the preferred embodiment. In a second modification, a torsion spring is also employed with a thumb screw (218) which permits the knee joint to be immobilized at any desired degree of flexion. In a second embodiment, an elbow brace (300) is provided for supporting and rehabilitation of the elbow joint and adjacent body portions in the arm. A hinge member (310) permits pivotal motion of the elbow brace about an axis corresponding to the axis of the elbow joint. A spring (334) provides a moment about the pivotal axis of the hinge member to inhibit the biceps muscle and provide a variable resistance to motion to rehabilitate the elbow joint and surrounding tissues.

17 Claims, 15 Drawing Figures

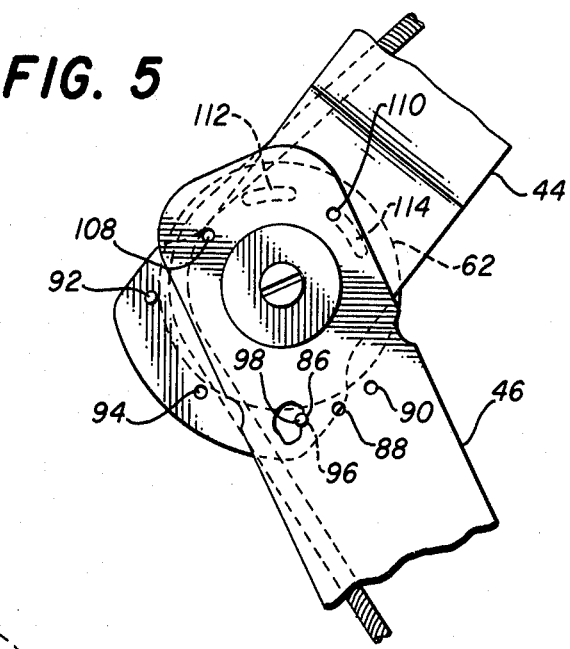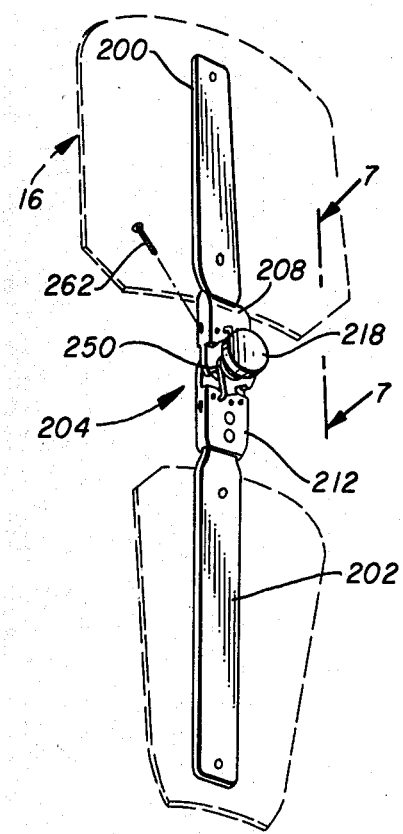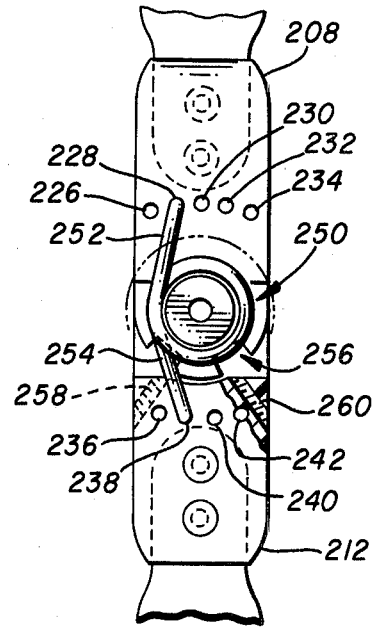

KNEE AND ELBOW BRACE

TECHNICAL FIELD

This invention relates to patient care, and in particular to the stabilization and rehabilitation of a joint.

BACKGROUND ART

Braces for immobilizing joints in the human body are known. With particular reference to the lower extremity, devices are known which range from a full double upright conventional metal brace for permanent use in a neuromuscularly disabled individual to a knee immobilizer which incorporates metal stays with a soft foam and cloth outer body for nonrigid immobilization of knees after injuries and minor surgeries.

The present cloth and metal knee immobilizer is inadequate for other purposes and often fails to provide good immobilization of the knee joint. For example, an individual will initially have approximately 15° to 20° of knee flexion due to fluid on the knee joint after injury or surgery. Therefore, it is very painful to attempt to straighten the knee acutely to fit an immobilizer.

A number of braces have been developed to control knee stability which incorporate a knee hinge. One cast brace is made from a variety of casting materials in which various types of hinges have been designed, some of which limit the motion within a specific arc. At the present time, some orthopedists repairing the medial collateral ligament position a postoperative splint or full long leg cast to hold the knee between 30° and 60° of flexion. This position is maintained for three to four weeks. A plaster type cast brace is then applied which has hinges incorporated therein to allow motion between a 30° to 60° arc from full extension. This brace is worn for another four week period at which time this brace is removed and a knee immobilizer is applied to stabilize the joint. There is a tremendous cost involved with multiple cast changes. In addition, a knee immobilizer is ultimately required at the end of the cast immobilization period.

An additional problem encountered with known knee immobilizers relates to properly positioning the immobilizer on a patient. The common immobilizer having medial and lateral stays sewn permanently to the device should ideally be placed along the mid-lateral line medially and laterally on the leg. However, this occurs only if the circumference of the leg is appropriate for the size immobilizer. Without appropriate fit, the medial and lateral stays become anterior to the knee joint axis if the device is too large. If the device is too small, the medial and lateral stays will be too far posterior to the knee. One immobilizer currently sold has movable medial and lateral stays, which somewhat improves the ability to properly position the immobilizer.

Another major problem with the known knee immobilizers are their inability to be positioned on a patient with a conical shaped thigh. This shape is the most common in individuals and therefore great difficulty arises in maintaining the immobilizer in the proper position. Finally, a knee immobilizer often does not provide rigid immobilization. A poor fit on a patient may permit flexure of the knee within a 30° arc.

SUMMARY OF THE INVENTION

In accordance with the present invention, a brace for supporting the regions adjacent a joint in the human body is provided. The brace includes first and second sections secured to the body on opposite sides of the joint. A hinge is interconnected between the first and second sections for pivotal motion about an axis substantially corresponding to the pivotal axis of the joint, the hinge permitting a pivotal motion between a preselected arc. A spring is provided for urging the first and second sections into a predetermined relationship to support the portions of the body about the joint in a desired relation.

In accordance with yet another aspect of the present invention, an elbow brace for supporting the regions adjacent the elbow is provided. The elbow brace includes first and second sections secured to the body on opposite sides of the elbow. A hinge interconnects the first and second sections for pivotal motion about an axis substantially corresponding to the pivotal axis of the elbow. Springs are interconnected between the first and second sections to urge the elbow into a desired position.

In accordance with yet another aspect of the present invention, a knee brace for support and rehabilitation of the knee joint and adjoining tissue is provided. The knee brace includes an upper leg section for attachment to the upper leg, the upper leg section being adjustable for use with a range of leg sizes. A lower leg section is provided for attachment to the lower leg, the lower leg section also being adjustable for use with a range of leg sizes. Hinges interconnect the upper and lower leg sections on each side of the knee joint, the hinges having a pivotal axis corresponding substantially to the pivotal axis of the knee joint. Locking structure is provided to lock the hinges in a set position to immobilize the knee joint. Limit structure is provided for limiting the pivotal motion of the hinges to permit the knee joint to move within a preselected arc. Springs interconnect the upper and lower leg sections for urging the hinges and knee joint to pivot to one preselected position.

DESCRIPTION OF THE DRAWINGS

A more complete understanding of the invention may be had by reference to the following Detailed Description when taken in conjunction with the accompanying Drawings, wherein:

FIG. 5 illustrates the hinge of the knee brace in flexion;

FIG. 6 is a perspective view of a first modification of the knee brace incorporating an alternate hinge;

FIG. 7 is a side view of the hinge in the first modification of the knee brace taken along line 7—7 in the direction of the arrows in FIG. 6;

DETAILED DESCRIPTION

Figure 3:
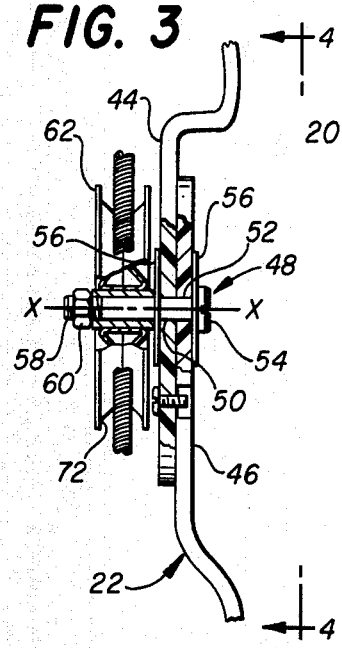
FIG. 3 is a vertical cross-sectional view of a hinge member for use in the knee brace.

Referring now to the Drawings, wherein like reference characters designate like or corresponding parts throughout several views, FIGS. 1–5 illustrate a first embodiment of the invention forming a knee brace 10.

The knee brace 10 incorporates three major features. The knee brace 10 may be used as a knee immobilizer which permits the knee to be rigidly set to a desired degree of flexion. The knee brace 10 may also be used as a mobilizer. The knee brace will permit the knee joint to be moved within a predetermined arc and the knee brace may also incorporate springs to assist the extension of the knee. Finally, the knee brace 10 may be used in rehabilitation by providing exercise in overcoming resistance from the springs.

The knee brace 10 includes flexible thigh and calf cuffs 12 and 14, and two substantially identical side members 15 and 16. The side members include rigid thigh and calf plates 17 and 18, and thigh and calf stays 20 and 22. The thigh and calf components are connected at hinge members 24 for pivotal motion about an axis X—X corresponding to the axis of pivotal motion of the knee joint 25 when the knee brace 10 is properly positioned on the leg of a patient. A number of thigh straps 26 and calf straps 28 are provided to secure the knee brace 10 to the leg of the patient.

The thigh and calf cuffs 12 and 14 are in direct contact with the patient and are thus made of an appropriate material which allows the skin to breathe so that it will not macerate. The outer portion of the cuffs 12 and 14 is preferably formed of a material having a plurality of loops receptive to engagement with a plurality of small hook-like members extending from an adjacent surface to secure the surface to the cuff. One example of this type of structure is distributed under the tradename Velcro. The cuffs 12 and 14 are wrapped about the thigh and calf of the patient, while leaving a midportion open adjacent the knee joint for dressings, bandages, etc.

Each of the side members 15 and 16 is then placed adjacent the cuffs 12 and 14 so that the pivotal axis of the hinge members 24 correspond to the pivotal axis of the knee joint. The thigh plates 17 and calf plates 18 are formed of a semirigid material, such as plastic, and are shaped generally to conform to the leg of the patient. On the inner surface of thigh plates 17 are mounted two strips 30 having hook-like members for engagement with the outer surface of the thigh cuff 12. Two strips 32 are similarly fastened on the inner surface of the calf plates 18 to engage the outer surface of the calf cuff 14. Both strips 30 and 32 may comprise Velcro fasteners.

The thigh plates 17 and calf plates 18 have a number of holes drilled therethrough to receive bolts 36 for mounting buckles 38 on the outer surface of the plate. Holes are drilled in each of the plates along the medial line thereof to accept bolts 40. The thigh stays 20 are secured to the thigh plates 17 by bolts 40. The calf stays 22 are secured to the calf plates 18 by bolts 40.

Figure 1:
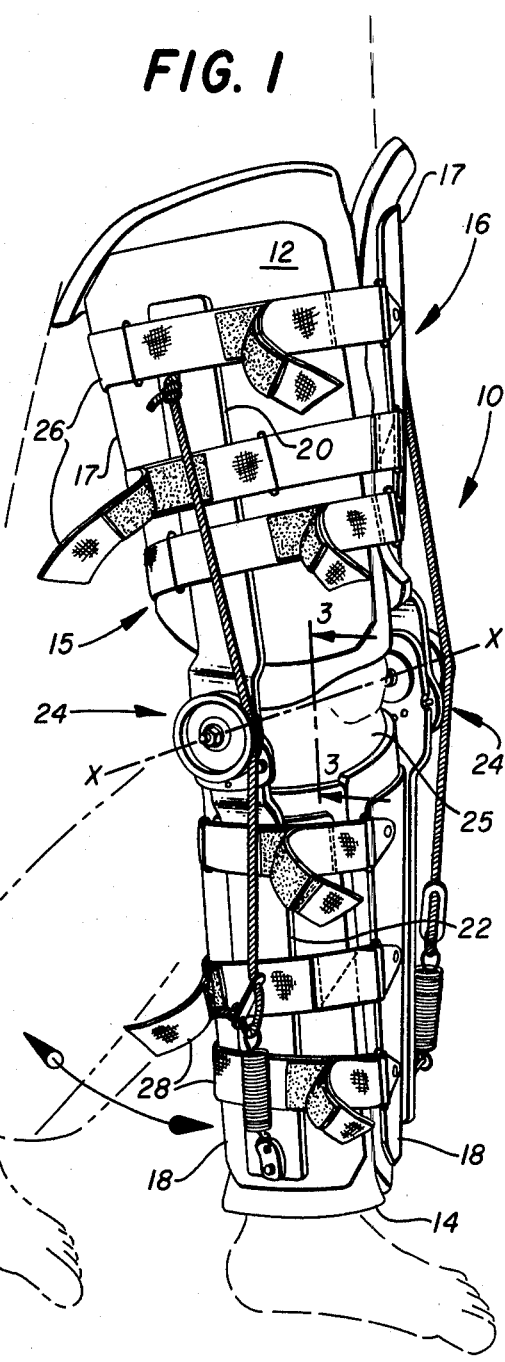
FIG. 1 is a perspective view of the first embodiment of the invention forming a knee brace.
Figure 2:
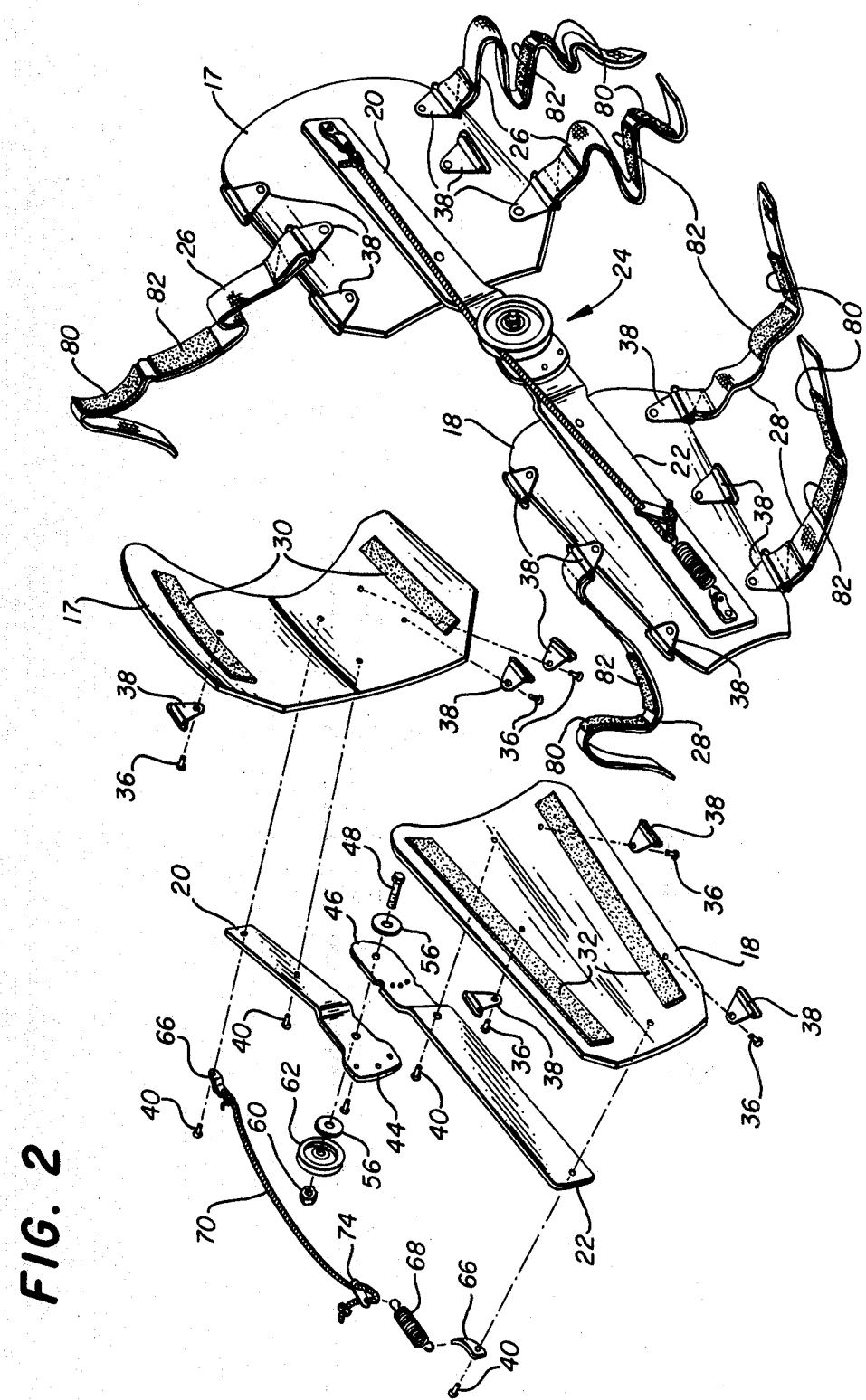
FIG. 2 is an exploded view of the knee brace.
Figure 8:
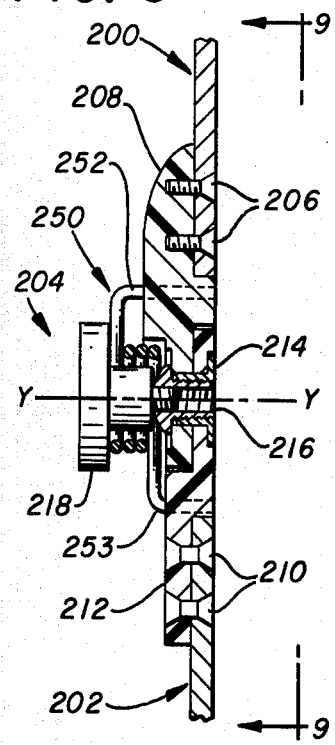
FIG. 8 is a vertical cross-sectional view of the hinge in the first modification of the knee brace.
Figure 9:
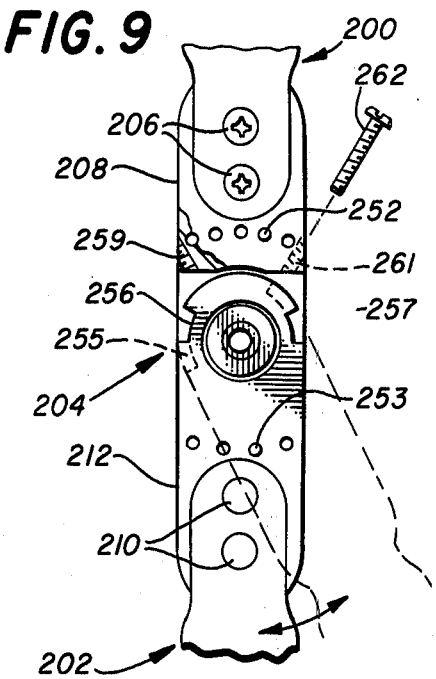
FIG. 9 is a side view of the hinge in the first modification of the knee brace taken along line 9—9 in the direction of the arrows in FIG. 8.

With reference to FIGS. 1–3, the lower portion of the thigh stays 20 include an offset hinge portion 44. The upper end of calf stays 22 include an offset hinge portion 46. A hinge pin 48 passes through apertures 50 and 52 in the hinge portions 44 and 46, respectively to define the pivotal axis X—X between the stays 20 and 22. The head 54 of hinge pin 48 abuts a washer 56 positioned on the inside of hinge portion 46. The end opposite head 54 includes a threaded portion 58 which extends outwardly of the outer surface of hinge portion 44. The hinge pin 48 is secured by a nut 60, pulley 62 and a second washer 56.

Two of the bolts 40 on each side member also fasten brackets 66 to the outer surface of the side member. The lower bracket 66 includes an outwardly turned portion having a hole therein for receiving one end of a spring 68. The upper bracket 66 has a similar outwardly turned portion with a hole to receive one end of a cord 70. The cord is connected adjacent its second end to the free end of spring 68. The midportion of the cord 70 is received in the groove 72 of pulley 62. A plate 74 having matching holes is used to tension the cord 70 as desired.

When positioning side members 15 and 16 on the leg of the patient, the center line of the plates 17 and 18 are positioned on the mid-lateral line on the sides of the leg. The side members may then be secured to the leg by inserting the thigh straps 26 and calf straps 28 through the suitable buckles 38. Each of the straps 26 and 28 may include a strip 80 having a plurality of hook-like members and a strip 82 having a plurality of loops to receive the hook-like members of strip 80. Again, the strips may be formed of Velcro material. While this is the preferred technique for fastening straps 26 and 28, any other suitable fasteners may be employed.

It is readily apparent from the discussion above and the accompanying drawings that the knee brace 10 may be employed on a range of leg sizes while maintaining the center line of each side member in correspondence with the mid-lateral lines of the leg. This overcomes the problem known in the prior art where the stays frequently are anterior or posterior of the mid-lateral line of the leg.

As noted previously, knee brace 10 may be used as an immobilizer for the knee joint. The knee brace 10 further permits the knee joint to be maintained at preselected angles of flexion. This feature is accomplished by the hinge members 24 in a manner described hereinafter.

The hinge portion 46 of calf stays 22 include three threaded apertures 86, 88 and 90 centered on a circle of given radius from the pivot axis and positioned at regular intervals along the circle. The hinge portion 44 of the thigh stays 20 includes threaded apertures 92, 94 and 96. The apertures 92, 94 and 96 are also centered along the circle of given radius from the pivot axis and are spaced regularly along the circle.

Figure 4:
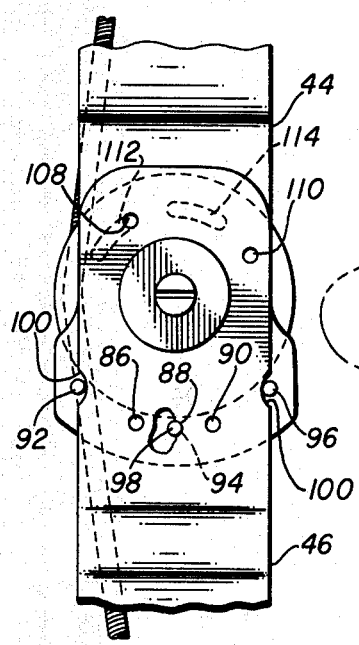
FIG. 4 is a side view of a hinge in the knee brace in the fully extended position.

If the leg of the patient to which knee brace 10 is applied is to be immobilized in the fully extended position, the hinge members 24 must be positioned as shown in FIG. 4. A threaded bolt 98 may be threaded through apertures 94 and 88 to prevent motion in the hinge members 24 from the extended position. The hinge members 24 also permit the knee joint to be immobilized at preselected angles of flexion. In one knee brace constructed under the teachings of the present invention, the apertures 86, 88 and 90 are separated by a 15° arc and the apertures 92, 94 and 96 are separated by a 45° arc. If, for example, a flexion of 60° is desired in the knee joint, the hinge members 24 would be fixed in the position illustrated in FIG. 5. In this position, apertures 86 and 96 will be aligned and a bolt 98 may be threaded through both apertures to immobilize the knee brace 10 at this angle. It is readily apparent that the knee brace 10 may be immobilized at any number of preselected angles limited only by the number of apertures in each hinge portion. The constructed knee brace permits flexion from 0° or full extension, to flexion at 15°, 30°, 45°, and 60° for immobilization.

It will be noted that the apertures are positioned in a symmetrical manner about the center line of the thigh and calf stays so that the side members 15 and 16 may be interchangeable from side to side of the leg of the patient or between the left and right leg of a patient. This reduces the cost of manufacture of knee brace 10.

The knee brace 10 also performs the function of a mobilizer. At the present time, a patient will proceed from a knee immobilizer to therapy to begin range of motion exercises to the knee joint after injury or surgery. The range of motion obtained in the knee joint is usually somewhat difficult at first. It is at times very painful for the individual to flex the knee joint after being immobilized in an extended position for a period of time. Most knee surgery involves incisions on the anterior aspect of the knee joint through the quadriceps expansion. Any tension on this structure will induce pain. This structure is attached to the quadriceps musculature in the anterior aspect of the thigh and any spasticity or spasm of the quadriceps muscle, or involuntary contraction, will put tension on the quadriceps expansion.

The knee brace 10 is designed with springs 68 and cords 70 to provide an extension assist to the patient. When cords 70 are tensioned by the springs, a moment is generated about axis X—X since cords 70 are offset from the axis by pulleys 62. Threaded bolts 98 may be threaded into apertures 92 when the hinge portions are positioned as shown in FIG. 4. The bolts 98 prevents the knee joint from overextending by abutting the surface of notches 100 formed in hinge portions 46. However, the hinge members 24 will permit flexion to any degree. The tension in springs 68 and cords 70 is adjusted by use of the plates 74 to induce a preselected tension in the fully extended position.

The tensioned cords 70 also provide resistance against which the hamstring muscles in the leg may work. The hamstring muscles are the muscles behind the knee which flex the knee. When the hamstring muscles are actively flexing against a resistance, a reflex inhibition of the neuro function to the quadriceps muscle is present. This allows the maximum relaxation of the quadriceps muscle when the patient is attempting to increase the range of motion in flexion. When the patient relaxes the hamstring muscles, the tensioned cords 70 will cause the knee brace 10 to pivot to the extended position and prevent the patient from using the painful quadriceps muscle during the postoperative state. This feature permits the earlier achievement of a painless range of motion after surgery on the knee joint.

The third feature of the knee brace 10 is its use in rehabilitation of the knee joint and leg of the patient. When the patient has gained adequate range of motion in the knee joint, the patient will typically undergo a series of exercises in an attempt to strengthen the quadriceps muscle. In the past, this exercise has typically been initiated by isometric exercises in which the knee is not taken through any range of motion. The exercise then progresses to straight leg lifting with weights on the ankle of the leg or to a limited arc motion against resistance such as provided by a weight training machine or other weights.

It is often counterproductive for the patient to begin at a full 90° flexion of the knee joint and extend the knee joint against weight. This action places a great deal of stress on the patella femoral joint behind the kneecap. Movement against resistance from approximately a 30° flexion to full extension is less harmful and provides a more beneficial exercise rehabilitation program.

Threaded apertures 108 and 110 are provided on the hinge portions 46 at a given radius from the pivotal axis. Two arcuate slots 112 and 114 are formed in the hinge portions 44 which are also centered about the pivotal axis. By inserting a threaded bolt 98 through apertures 108 and into slots 112, the range of motion of a knee brace 10 will be limited between a predetermined arc, as between 0° and 30° flexion. By pivoting the hinge members 24 to a 30° flexion, a threaded bolt 98 may be threaded through apertures 110 and into slots 114 to limit the pivotal motion to a second predetermined arc, as from 30° to 60° flexion.

If the knee is to be exercised between 0° and 30°, the knee brace 10 may be set accordingly. By moving the cords 70 so as to be received in grooves 72 of pulleys 62 posterior to the knee joint, the tension in cords 70 resist the extension of the leg. The tension cords 70 would urge the knee brace 10 and patient's leg into a 30° flexion. The patient would then be required to exercise the quadriceps muscles to achieve full extension of the knee joint. This would provide a reasonably specific and repeatable resistance through which the patient may do quadriceps exercises. The tension of cords 70 may be adjusted to vary the resistance.

A first modification of the knee brace 10 is illustrated in FIGS. 6-9. Each of the side members 15 and 16 is provided with a thigh stay 200 and calf stay 202 which are somewhat modified from thigh stay 20 and calf stay 22. In addition, the first modification includes hinge members 204 which have some structural differences from hinge members 24 but operate in substantially the same manner. While the hinge members 24, cords 70 and springs 68 are adequate to perform the functions described hereinabove, the first modification of the knee brace 10 forms the preferred construction.

The lower end of each thigh stay 200 includes apertures for accepting threaded screws 206 to secure hinge portion 208 thereto. The upper end of each calf stay 202 has apertures to accept rivets 210 mounting a lower hinge portion 212 thereon.

The upper hinge portion 208 and lower hinge portion 212 are interconnected for pivotal motion about axis Y—Y. When the knee brace 10 is mounted on the leg of a patient, the axis Y—Y will correspond to the pivotal axis of the knee joint. The hinge portions are secured in this relationship by sleeve 214 having a smooth outer surface acting as a bearing and a threaded inner surface, and a bolt 216 threadedly received within the sleeve 214. The bolt 216, in turn, preferably has a threaded central core adapted to receive the threaded end of a thumb screw 218.

The upper hinge portion 208 has apertures 226, 228, 230, 232 and 234 formed therein all lying on a circle of given radius from the pivotal axis Y—Y and equally spaced apart on the circle. The lower hinge portion has similar apertures 236, 238, 240, and 242 formed therein lying on the identical circle and equally spaced. The apertures 226-234 are adapted to receive the first leg 252 of a torsion spring 250. The second leg 253 of the torsion spring is received in one of the apertures 236-242. The torsion spring 250 is retained with its legs in engagement with apertures and centered about the pivotal axis by contact with the thumb screw 218.

The upper hinge portion 208 also includes two slots 254 and 256 at the outer end thereof. These slots are positioned in alignment with oblique threaded holes 258 and 260 in the lower hinge portion 212 within a predetermined range of flexion. The threaded holes 258 and 260 are adapted to receive a threaded screw 262 in a similar manner to that shown in FIG. 9. As can readily be seen, the hinge member 204 is reversible and may be used on either side of the knee, or either leg.

The lower hinge portion 212 includes slots 255 and 257 at the outer end thereof. These slots are aligned with oblique threaded holes 259 and 261 in upper hinge portion 208 within a predetermined range of flexion. The threaded holes 259 and 261 are adapted to receive a screw 262.

The first modification of knee brace 10 performs substantially all the functions described hereinabove. The bolt 216 is constructed of a material, such as plastic, with some resiliency so that the thumb screws 218 on both side members of the knee brace may be tightened to deform the bolts and prevent pivotal motion between the two hinge portions. The knee joint of the patient may then be immobilized at a desired degree of deflection by merely tightening the thumb screw 218. When knee brace 10 is employed as an immobilizer, the torsion springs 250 need not be in place in the apertures.

The slots 254 and 256 are preferably sized and positioned so that a bolt threaded through bolt hole 258 or 260 will be received within slot 254 or 256 when the angle of flexion of the knee is between 0° and 30°. The slots 255 and 257 are sized and positioned so that a bolt 262 extending through threaded hole 259 or 261 will enter the slot when the angle of flexion of the knee joint is between 30° and 60°. Therefore, a limited range of motion is provided, at whatever arc desired, by properly sizing slots 254-257.

By positioning the torsion spring 250 within the apertures so that the spring creates a moment about the pivotal axis and urges the knee joint to full extension, a knee mobilizer is provided which relieves the necessity to exert the quadriceps muscles. The degree of spring tension may be adjusted by moving the legs 252 and 253 to different apertures.

The torsion spring 250 may also be used to resist motion in either direction in the arc determined by slots 254-257. The resistance in one direction is readily transformed to resistance in the opposite direction by removing the thumb screw 218 and reversing the positioning of the torsion spring 250 on the hinge portions.

While the use of a torsion spring such as 250 is the preferred construction, the tension cord 70 or any other provisions for creating a moment about the pivotal axis would be suitable for use in the knee brace 10. For example, memory rods may be used to provide the moment. Rubber bands may also be interconnected between the hinge portions in either side member 15 or 16 to provide the moment.

Figure 10:
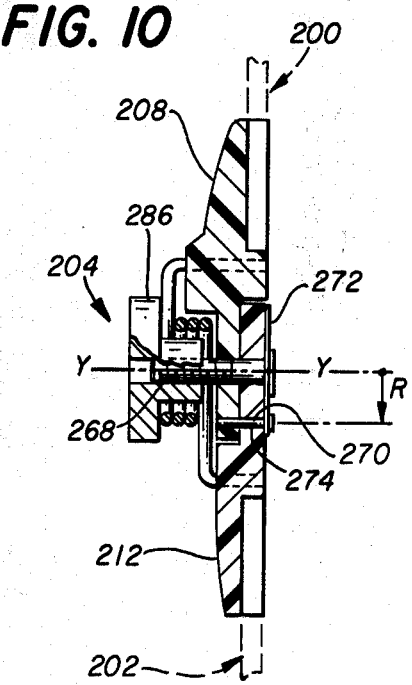
FIG. 10 is a vertical cross-sectional view of a hinge in the second modification of the knee brace.
Figure 11:
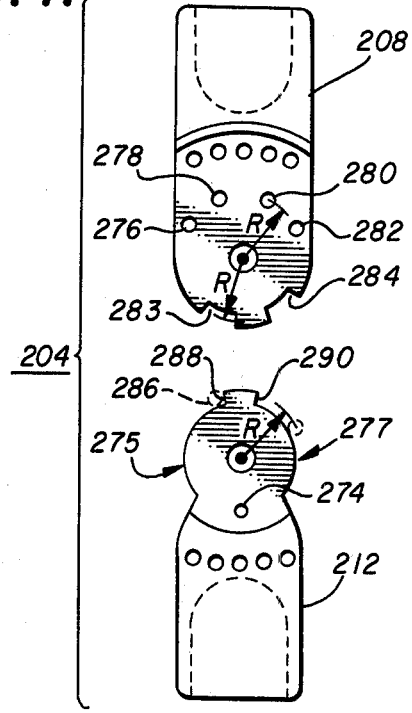
FIG. 11 is a side view of the upper and lower members of the hinge in the second modification of the knee brace.

In a second modification of the knee brace 10 illustrated in FIGS. 10 and 11, the threaded holes 258-261, sleeve 214 and bolt 216 are eliminated. A threaded bolt 268 and pin 270 are mounted on a backing plate 272 with centers at a distance R apart. The threaded bolt 268 passes through the hinge portions to provide pivotal motion about the axis Y—Y. The pin 270 extends either through an aperture 274 or adjacent surfaces 275 or 277 formed in the lower hinge portion 212. The pin extends from the opposite side of the lower hinge portion and may be received in one of apertures 276, 278, 280 and 282. A series of slots 283 and 284 are also provided in the upper hinge portion. To limit the arc from full extension to a desired flexion, a pin 286 is passed through either apertures 278 or 280 to abut against surfaces 288 or 290 to prevent overextension. The pin 270 is then positioned in the aperture providing the desired flexion. For example, pin 270 may pass through aperture 282 to provide 0° to 30° flexion. The knee joint may be immobilized at varied degrees of flexion by positioning pin 270 and one or more pins 286. Slots 283 or 284 are formed within the upper hinge portion to limit arc motion in cooperation with pin 270, from 30° to 60° flexion for example. Each of the apertures and slots are centered at a distance R from the pivotal axis of the hinge member. The apertures and slots are again adapted so that the pin 270 will permit the knee brace 10 to be immobilized at predetermined degrees of deflection and also limited in pivotal motion in a given arc. A modified thumb screw 288 is threaded onto the end of bolt 268 to maintain the bolt and pin 270 in engagement with the hinge portions and may be used to tighten bolt 268 to immobilize the knee.

A second embodiment of the present invention is illustrated in FIGS. 12-15 and forms an elbow brace 300. The elbow brace 300 is adapted for supporting the elbow and adjoining tissue on a patient's arm 304. The elbow brace generally includes three major sections. The upper arm section 306 is interconnected to the lower arm section 308 by a hinge member 310.

Figure 12:
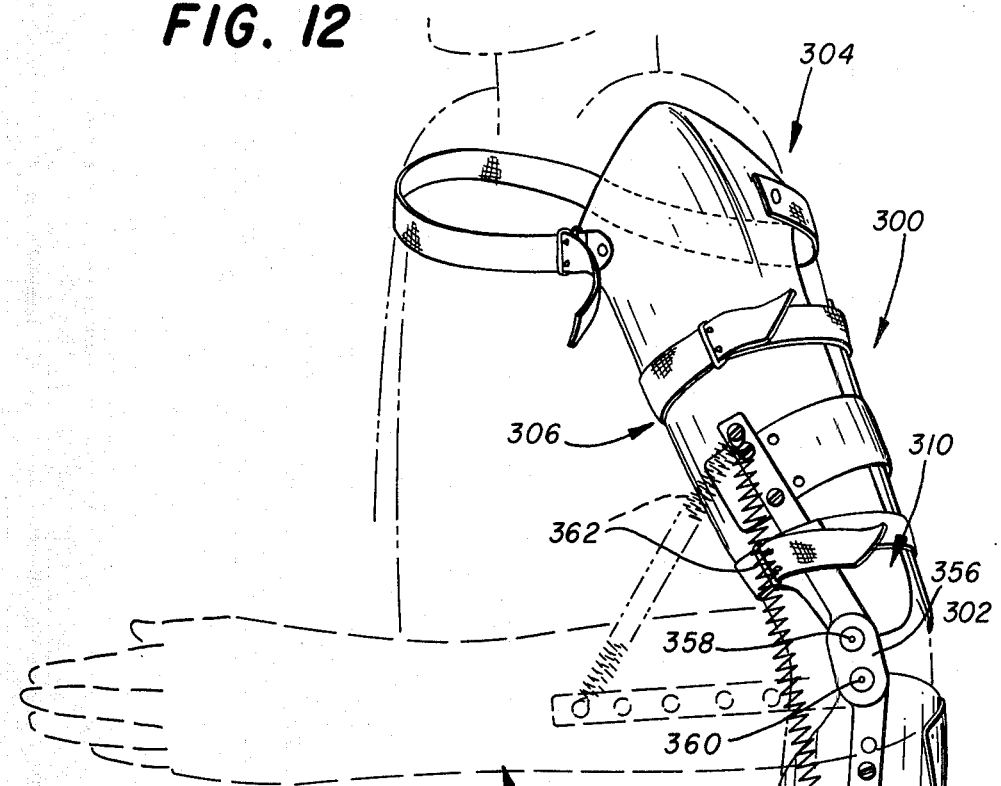
FIG. 12 is a perspective view of a second embodiment of the present invention comprising an elbow brace.

The upper arm section 306 includes an outer plate 312 shaped to fit over the outside of the upper arm and shoulder. An inner plate 314 is shaped to fit the inner part of the upper arm adjacent the chest. An interconnecting member 316 is riveted to both plates 312 and 314 by rivets 318. In the preferred construction, the plates 312 and 314 and member 316 are formed of semi-rigid material, such as plastic. Straps 320 including buckles 322 at one end are provided to strap the plates 312 and 314 about the upper arm portion. A shoulder strap 324 is provided to wrap about the shoulders of the patient and to a buckle 322 thereon to further support the plates on the patient as shown in FIG. 12.

The lower arm section 308 includes a back plate 330 and a front plate 332 which cooperate to substantially encase the lower arm of the patient. In the preferred embodiment, one of the plates, such as back plate 330, has strips 334 secured thereon including loops for interlocking with flexible hooks on straps 336 attached to the other plate. Again, the strips 334 and straps 336 may comprise the fastener known as Velcro. However, any suitable means for securing the plates 312 and 314 and 330 and 332 would be adequate.

An upper arm stay 240 is secured to both outer plate 312 and member 316 by a number of threaded bolts 342. A lower arm stay 344 is secured to the back plate 330 by screws 342.

Figure 14:
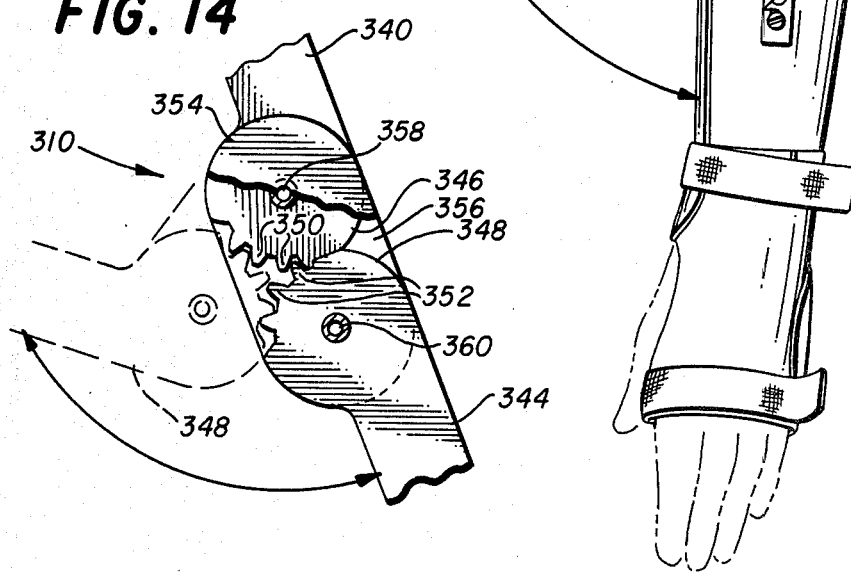
FIG. 14 is a side view of the hinge used in the elbow brace.
Figure 13:
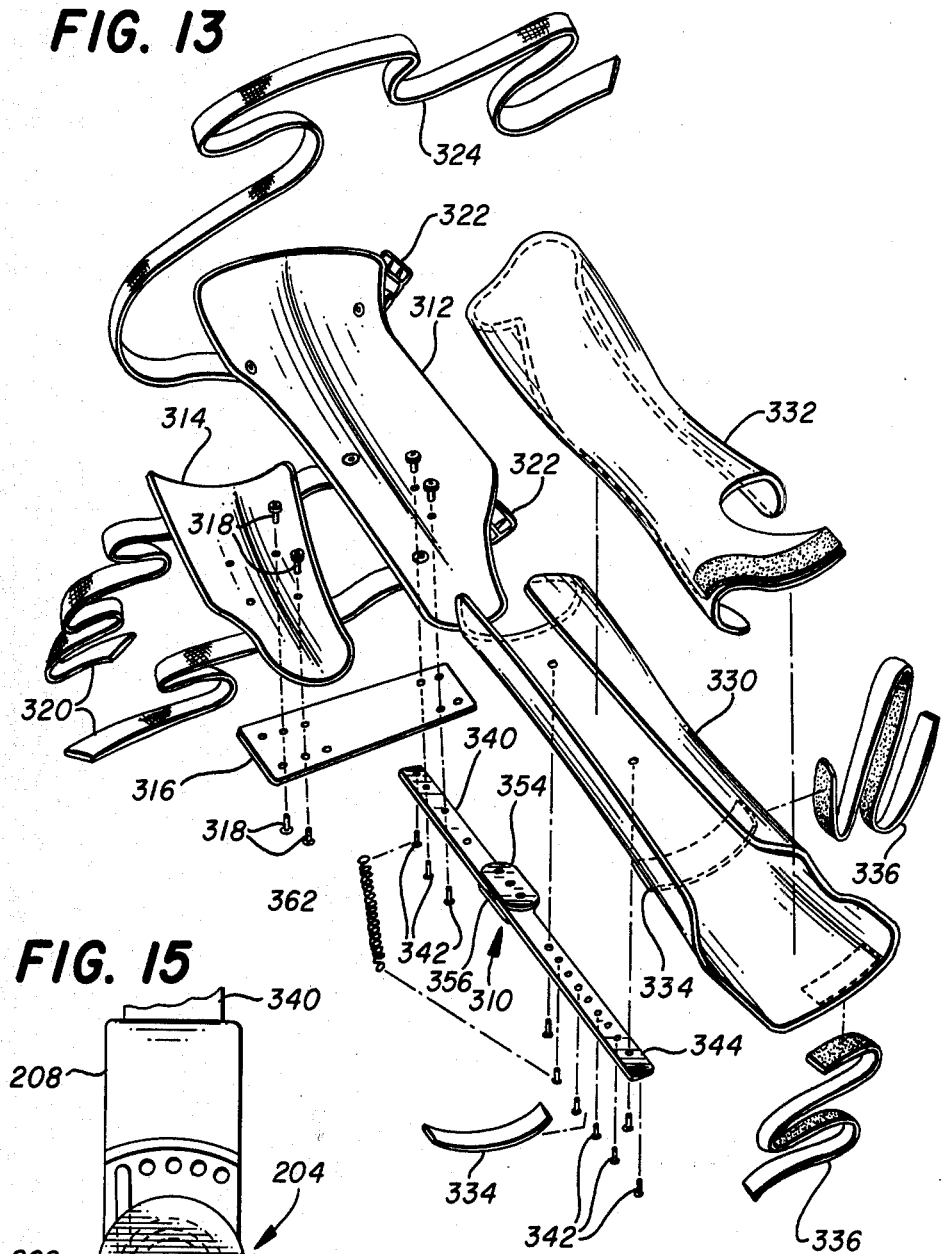
FIG. 13 is an exploded view of the elbow brace.

The hinge member 310 interconnects the stays 340 and 344 for pivotal motion about an axis corresponding substantially to the pivotal axis of the elbow and forms a polycentric hinge. The stays 340 and 344 each end in portion 346 and 348 having interlocking gear teeth 350 and 352 as best shown in FIG. 14. Plates 354 and 356 are secured on either side of the end portions of the stays and are pivotally mounted thereto by pins 358 and 360. The pivotal motion of the hinge member 310 is illustrated in FIG. 14. The full line corresponds to the position of the hinge member when the arm is fully extended and the dotted line represents the position of stay 344 when the elbow has been flexed.

A coiled spring 362 is interconnected between bolts and screws 342 on the upper and lower arm stays 340 and 344 respectively. The spring urges the elbow brace 300 and arms 304 into the bent position illustrated in phantom line in FIG. 12. This position represents the most suitable position for recovery from injury or surgery. The spring also acts to exercise the tricep muscles at the posterior of the upper arm while inhibiting contraction of the bicep muscles.

Figure 15:
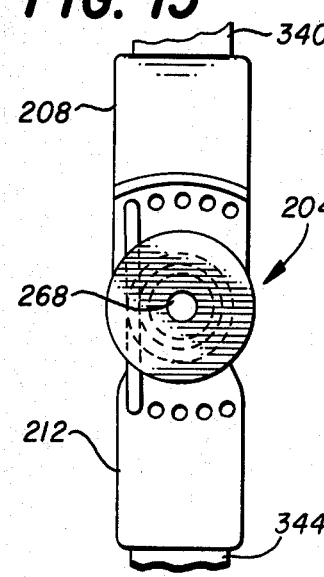
FIG. 15 is a side view of a hinge used in a first modification of the elbow brace.

In the first modification of elbow brace 300, illustrated in FIG. 15, a hinge member 204 replaces the hinge member 310 and spring 362. The hinge member 204 permits reduction in the size of the hinge member.

Although two embodiments of the invention have been illustrated in the accompanying drawings and described in the foregoing Detailed Description, it will be understood that the invention is not limited to the embodiments disclosed, but is capable of numerous rearrangements, modifications and substitutions of parts and elements without departing from the scope of the spirit of the invention.

We claim:

1. The knee brace comprising:
   a thigh plate shaped to conform to the thigh of the leg;
   a calf plate shaped to conform to the calf of the leg;
   said thigh plate and calf plate being positioned on the thigh and calf when the knee brace is mounted on the leg so that the center lines of said thigh and calf plates lie on the mid-lateral line of the leg;
   a thigh stay secured on the outer surface of said thigh plate and extending to a first hinge portion of a hinge moment adjacent the knee joint when positioned on the leg;
   a calf stay secured on the outer surface of said calf plate and extending to a second hinge portion of said hinge member adjacent the knee joint when positioned on the leg;
   means for limiting the pivotal motion of said hinge member to confine the motion of the joint within a preselected arc including an arc of zero degrees to immobilize the knee and for establishing a predetermined angular relationship between the hinge portions and thereby controlling the degree of flexion of the knee;
   spring means interconnecting said upper and lower sections for creating a moment about the pivotal axis of said hinge member for urging said upper and lower sections toward a predetermined relationship;
   fastening means for securing the thigh and calf plates to the leg.

2. The brace of claim 1 wherein said spring means permits variation of the moment about said hinge member and permits reversal of the moment.

3. The brace of claim 1 wherein said hinge member includes first and second hinge portions interconnected for pivotal motion about the pivotal axis, said first and second hinge portions each having at least one aperture formed therein, the apertures in both of said hinge portions being aligned at the preselected degree of flexion of the joint; and
   said limiting means comprising a locking pin for insertion through the aligned apertures to prevent pivotal motion and immobilize the knee.

4. The brace of claim 1 wherein said hinge member includes first and second hinge portions interconnected for pivotal motion about the pivotal axis, said first and second hinge portions each having at least one aperture formed therein, at least one of the apertures forming a curvalinear slot having a radius centered on the pivotal axis; and
   said limiting means including a limit pin inserted through the apertures in said first and second hinge portions to limit the pivotal motion of the hinge member about the pivotal axis.

5. The brace of claim 1 wherein said spring means comprises a torsion spring, one end of said torsion spring being secured to the upper section and the opposite end being secured to said lower section to create a moment about the pivotal axis.

6. The brace of claim 1 wherein said hinge member includes first and second hinge portions interconnected for pivotal motion, each of said hinge portions having a plurality of apertures formed therein equidistant from the pivotal axis; and
   said spring means comprising a torsion spring, the ends of said torsion spring being received in selected ones of the apertures in said first and second hinge portions to achieve a desired moment about the pivotal axis.

7. The brace of claim 1 wherein said spring means comprises:
   a cord fastened at one end to the upper section;
   a spring secured between the opposite end of said cored and said lower section;
   a pulley secured to said hinge member and centered on the pivotal axis for guiding the cord to create a moment about the pivotal axis when said cord is in tension; and
   means for varying the length of the cord to vary the tension induced in the cord by said spring to vary the moment about said hinge member.

8. A knee brace for supporting the knee joint in a leg comprising:
   a thigh cuff for wrapping about the thigh of the leg;
   a calf cuff for wrapping about the calf of the leg;
   first and second side members for being secured to said thigh and calf cuffs on the mid-lateral line of the leg, said first and second side members each including:
   a thigh plate adapted to be secured to said thigh cuff, said thigh plate being shaped to conform to the thigh of the leg;
   a calf plate adapted to be secured to said calf cuff, said calf plate being shaped to conform to the calf of the leg;
   both said thigh plate and calf plate being positioned on the thigh and calf cuffs when wrapped about the leg so that the center line of said thigh and calf plates lie on the mid-lateral line of the leg;
   a thigh stay secured on the outer surface of said thigh plate and extending to a first hinge portion adjacent the knee joint when positioned on the leg;
   a calf stay secured on the outer surface of said calf plate and extending to a second hinge portion adjacent the knee joint when positioned on the leg;

hinge pin means for interconnecting said first and second hinge portions to permit pivotal motion about an axis substantially corresponding to the pivotal axis of the knee joint when positioned on the leg;

means for limiting the pivotal motion between said first and second hinge portions for restricting the motion of the knee joint within a preselected arc including an arc of zero degrees wherein the knee is immobilized and for establishing a predetermined angular relationship between the hinge portions and thereby controlling the degree of flexion of the knee;

spring means interconnected between said thigh stay and calf stay for creating a movement about the pivotal axis to urge the knee joint into a desired degree of flexion; and fastening means for securing said first and second side members, and said thigh and calf cuffs to the leg.

9. The knee brace of claim 8 wherein said spring means in each of said first and second side members permits variation of the moment about the pivotal axis to vary the force exerted urging the knee joint into the desired degree of flexion.

10. The knee brace of claim 8 wherein said first and second hinge portions in each of said first and second side members has at least one aperture formed therein;
said limiting means comprising a locking pin for insertion through aligned apertures in said first and second hinge portions to prevent pivotal motion about the pivot axis and immobilize the knee joint at a desired degree of flexion.

11. The knee brace of claim 8 wherein each of said first and second hinge portions in each of said first and second side members has at least one aperture formed therein, at least one of the apertures defining an elongated curvalinear slot having a radius centered on the pivotal axis; and
said limiting means including a limit pin for insertion through the apertures to limit the pivotal motion about the pivotal axis to restrict the motion of the knee joint within the preselected arc.

12. The knee brace of claim 8 wherein each of said first and second hinge portions in each of said first and second side members have a plurality of apertures formed therein;
said spring means including a torsion spring centered on the pivotal axis, each end of the torsion spring being positioned in an aperture in one of said hinge portions to create a moment about the pivotal axis.

13. The knee brace of claim 8 wherein the spring means in each of said first and second side members comprises:
a cord fastened at one end to said thigh stay;
a spring secured between the opposite end of said cord and said calf stay;
a pulley centered on the pivotal axis and guiding said cord offset from the pivotal axis so that tension in said cord creates a moment about the pivotal axis; and
means for varying the length of said cord to vary the moment about the pivotal axis.

14. An elbow brace for supporting the elbow joint and adjacent body portions, comprising:
an upper arm section adapted to be secured to the upper arm;
a lower arm section adapted to be secured to the lower arm;
a hinge member interconnecting said upper and lower arm sections for pivotal motion about a pivotal axis, the pivotal axis corresponding substantially to the pivotal axis of the elbow joint when said upper and lower arm sections are secured to the arm; and
spring means interconnected between said upper and lower arm sections to create a moment about the pivotal axis to urge the elbow joint into a desired degree of flexion when said elbow brace is secured to the arm.

15. The elbow brace of claim 14 wherein said hinge member comprises a polycentric hinge having a variable axis of pivotal motion.

16. An elbow brace for supporting the elbow joint and regions adjacent thereto in an arm, comprising:
outer and inner upper arm plates shaped to conform to portions of the upper arm;
at least one strap for securing said outer and inner upper arm plates to the upper arm;
front and back lower arm plates shaped to conform to portions to the lower arm;
at least one strap for securing said front and back lower arm plates to the lower arm;
an upper arm stay secured to said outer upper arm plate and having a hinge portion extending adjacent the elbow joint when secured on the arm;
a lower arm stay secured to said back lower arm plate and having a hinge portion extending adjacent the elbow joint when secured to the arm;
means for pivotally interconnecting the hinge portions of said upper and lower arm stays for pivotal motion about an axis corresponding substantially to the pivotal axis of the elbow joint when secured on the arm; and
a spring mounted at each end to a portion of said upper and lower arm stays and offset from the pivotal axis of said hinge portions thereof to generate a moment about the pivotal axis to urge the elbow joint into a degree of flexion desired.

17. The elbow brace of claim 16 wherein the hinge portions of said upper and lower arm stays are interconnected for pivotal motion about a polycentric axis.

* * * * *

UNITED STATES PATENT AND TRADEMARK OFFICE
CERTIFICATE OF CORRECTION

PATENT NO : 4,370,977
DATED : Feb. 1, 1983
INVENTOR(S): Mauldin et al.

It is certified that error appears in the above-identified patent and that said Letters Patent is hereby corrected as shown below:

Column 5, line 39, change "prevents" to --prevent--.

Column 5, lines 40-41, change "surface" to --surfaces--.

Column 6, line 31, change "muscles" to --muscle--.

Column 9, line 41, change "moment" to --member--.

Column 9, lines 54-55, change "upper and lower sections" to --first and second hinge portions--.

Column 9, lines 56-57, change "upper and lower sections" to --first and second hinge portions--.

Column 12, line 35, change "to" to --of--.

Signed and Sealed this

Tenth Day of November 1998

Attest:

Attesting Officer

BRUCE LEHMAN

Commissioner of Patents and Trademarks